United States Patent
Ohno et al.

(10) Patent No.: US 6,274,782 B1
(45) Date of Patent: Aug. 14, 2001

(54) METHOD FOR PURIFYING HEXAFLUOROETHANE

(75) Inventors: Hiromoto Ohno; Tetsuo Nakajo; Toshio Ohi; Tatsuharu Arai, all of Kawasaki (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 09/523,966

(22) Filed: Mar. 13, 2000

Related U.S. Application Data

(63) Continuation-in-part of application No. 09/001,536, filed on Dec. 31, 1997, now abandoned.

(30) Foreign Application Priority Data

Apr. 16, 1997 (JP) .................................................. 9-098891

(51) Int. Cl.⁷ ...................................................... C07C 17/38
(52) U.S. Cl. .............................................................. 570/179
(58) Field of Search ............................................... 570/179

(56) References Cited

U.S. PATENT DOCUMENTS 5,523,499    6/1996    Corbin et al. .

*Primary Examiner*—Alan Siegel
(74) *Attorney, Agent, or Firm*—Sughrue, Mion, Zinn, Macpeak & Seas, PLLC

(57) ABSTRACT

A purification method for purifying hexafluoroethane, comprising a step of making hexafluoroethane containing impurities of hydrofluorocarbons including two carbon atoms in a molecule contact a zeolite having a mean micropore size in a range of 3.5 Å to 11 Å and a silicon/aluminum ratio of not more than 1.5 or an adsorbent comprising the above-described zeolite and a carbonaceous adsorbent having a mean micropore size in a range of 3.5 Å to 11 Å, thereby reducing said hydrofluorocarbons.

9 Claims, No Drawings

METHOD FOR PURIFYING HEXAFLUOROETHANE

RELATD APPLICATIONS

This is a continuation-in-part of Application Ser. No. 09/001,536 filed on Dec. 31, 1997, now abandoned.

BACKGROUND OF THE INVENTION

1. Field of the Invention

The present invention relates to a method for purifying hexafluoroethane (hereinafter referred to as "FC-116" or "$CF_3CF_3$") and, more particularly, to a method for purifying FC-116 containing, as impurities, hydrofluorocarbons including two carbon atoms in a molecule (hereinafter referred to as "HFCs"), thereby reducing the impurities of HFCs.

2. Related Background Art

FC-116 is used, for example, for dry etching of semiconductor and, therefore, high-purity FC-116 is demanded.

Various methods have been proposed heretofore as to methods for producing this FC-116.

Specific examples of the methods well known include (1) electrolytic fluorination using ethane and/or ethylene as a raw material, (2) thermal decomposition for thermally decomposing tetrafluoroethylene or the like, (3) methods for fluorinating acetylene, ethylene, and/or ethane by use of metal fluoride, (4) methods for fluorinating dichlorotetrafluoroethane or chloropentafluoroethane or the like by use of hydrogen fluoride, (5) direct fluorination for letting fluorine gas react with ethane or a hydrofluorocarbon, and so on.

However, when FC-116 is produced by these methods, FC-116 as an objective product forms an azeotropic mixture or an azeotrope-like mixture with intermediates or by-products produced in reactions to FC-116 or with the hydrofluorocarbon used as a raw material. Therefore, the problem is that separation of FC-116 is extremely difficult.

For solving this problem, an example proposed is a purification method of FC-116 for treating FC-116 containing the impurities of chlorotrifluoromethane ($CClF_3$) and/or trifluoromethane ($CHF_3$) including one carbon atom with an adsorbent such as active carbon or a zeolite (U.S. Pat. No. 5,523,499).

There existed, however, no easy, economical, industrially advantageous method for purifying FC-116 containing the impurities of HFCs including two carbon atoms in a molecule and thereby producing high-purity FC-116 little containing the HFCs.

SUMMARY OF THE INVENTION

An object of the present invention is to provide a purification method of FC-116 capable of readily, economically, and industrially advantageously obtaining high-purity FC-116 little containing the impurities of HFCs by making FC-116 containing the HFCs including two carbon atoms in a molecule contact an adsorbent to adsorptively remove the HFCs.

The inventors conducted extensive and intensive studies in order to solve the above problem and came to find that when, in a process for producing high-purity FC-116, FC-116 containing the HFCs was made to contact a zeolite having a specific mean micropore size and a specific silicon/aluminum ratio (Si/Al), or an adsorbent comprising the above-described zeolite and a carbonaceous adsorbent (molecular sieving carbon) having a specific mean micropore size, the HFCs were able to be selectively adsorptively removed and high-purity FC-116 little containing the HFCs could be obtained, thereby accomplishing the present invention.

Specifically, the present invention provides a purification method for purifying hexafluoroethane (FC-116), comprising a step of making hexafluoroethane (FC-116) containing impurities of hydrofluorocarbons (HFCs) including two carbon atoms in a molecule contact a zeolite having a mean micropore size in a range of 3.5 Å to 11 Å and a silicon/aluminum ratio of not more than 1.5 or an adsorbent comprising the above-described zeolite and a carbonaceous adsorbent having a mean micropore size in a range of 3.5 Å to 11 Å, thereby reducing the hydrofluorocarbons (HFCs).

In the purification method of the present invention, the hydrofluorocarbons (HFCs) are preferably at least one compound selected from the group consisting of fluoroethane, 1,1-difluoroethane, 1,1,1-trifluoroethane, 1,1,1,2-tetrafluoroethane, 1,1,2,2-tetrafluoroethane, and pentafluoroethane. Further, FC-116 may include at least one fluorine-containing unsaturated compound selected from a group consist of tetrafluoroethylene, trifluoroethylene, 1,1-difluoroethylene, 1,2-difluoroethylene and monofluoroethylene as the HFCs.

In the purification method of the present invention, the hexafluoroethane (FC-116) containing the impurities of the hydrofluorocarbons (HFCs) including two carbon atoms in a molecule is preferably hexafluoroethane (FC-116) produced by a direct fluorination method for letting fluorine gas react with a hydrofluorocarbon including two carbon atoms in a molecule.

DESCRIPTION OF THE PREFERRED EMBODIMENTS

When the method for producing FC-116 is, for example, a direct fluorination method for letting fluorine gas ($F_2$) react with fluoroethane (hereinafter referred to as $C_2H_5F$ or as $CH_2FCH_3$ or "HFC-161") which is a hydrofluorocarbon including two carbon atoms in a molecule, reactions represented by formula (1) to formula (5) below, take place in addition to the principal reaction represented by formula (6) below.

$$C_2H_5F + F_2 \rightarrow C_2H_4F_2 + HF \quad \text{formula (1)}$$

$$C_2H_4F_2 + F_2 \rightarrow C_2H_3F_3 + HF \quad \text{formula (2)}$$

$$C_2H_3F_3 + F_2 \rightarrow C_2H_2F_4 + HF \quad \text{formula (3)}$$

$$C_2H_2F_4 + F_2 \rightarrow C_2HF_5 + HF \quad \text{formula (4)}$$

$$C_2HF_5 + F_2 \rightarrow C_2F_6 + HF \quad \text{formula (5)}$$

$$C_2H_5F + 5F_2 \rightarrow C_2F_6 + 5HF \quad \text{formula (6)}$$

In addition to FC-116 as an objective product, HFCs including two carbon atoms in a molecule, such as difluoroethane ($C_2H_4F_2$) trifluoroethane ($C_2H_3F_3$), tetrafluoroethane ($C_2H_2F_4$), pentafluoroethane ($C_2HF_5$, which will be referred to hereinafter as "HFC-125" or "$CF_3CHF_2$"), are produced as intermediates to FC-116.

In ordinary cases, 1,1-difluoroethane (hereinafter referred to as "HFC-152a" or "$CHF_2CH_3$") is produced in a greater amount among the difluoroethanes, 1,1,1-trifluoroethane (hereinafter referred to as "HFC-143a" or "$CF_3CH_3$") is produced in a greater amount among the trifluoroethanes, and 1,1,1,2-tetrafluoroethane (hereinafter referred to as "HFC-134a" or "$CF_3CH_2F$") is produced in a greater amount among the tetrafluoroethanes.

Below listed are boiling points of FC-116 as an objective product and the HFCs as intermediates under the atmospheric pressure.

HFC-152a ($CHF_2CH_3$)–24.2° C.
HFC-134a ($CF_3CH_2F$)–26.5° C.
HFC-161 ($CH_2FCH_3$)–37.1° C.
HFC-143a ($CF_3CH_3$)–47.4° C.
HFC-125 ($CF_3CHF_2$)–48.6° C.
FC-116 ($CF_3CF_3$)–78.1° C.

FC-116 and HFC-134a form an azeotrope-like mixture and FC-116 and HFC-125 form another azeotrope-like mixture. HFC-143a, HFC-161, and HFC-152a are materials very hard to separate from FC-116 by distillation. Therefore, the normal distillation operation involves countermeasures of increasing the number of steps of distillation column or increasing the number of distillation columns in order to minimize these impurities, but such countermeasures are uneconomical. rn addition, it is extremely difficult to produce high-purity FC-116 little containing the HFCS.

For selectively adsorptively removing the HFCs in FC-116, a zeolite having a mean micropore size in the range of 3.5 Å to 11 Å and the silicon/aluminum ratio of not more than 1.5 is axed am the adsorbent in the present invention.

The zeolite may be used singly, or two or more kinds of the zeolite may be used in combination at any ratio.

Further, for selectively adsorptively removing the HFCs (including the fluorine-containing unsaturated compounds) in FC-116, an adsorbent comprising the above-described zeolite and a carbonaceous adsorbent having a mean micropore size in the range of 3.5 Å to 11 Å can be used.

The mixing ratio of the zeolite to the carbonaceous adsorbent is preferably not less than 1.0 by weight.

Specific examples of the HFCs that can be removed by these adsorbents are at least one compound selected from HFC-161, HFC-152a, HFC-143a, 1,1,2,2-tetrafluoroethane (hereinafter referred to as "HFC-134" or "$CHF_2CHF_2$"), HFC-134a, HFC-125, and so on. Among these, the HFCs that can be removed by the above adsorbents are preferably a compound or compounds selected from HFC-134, HFC-134a, and HFC-125, and more preferably HFC-134a and/or HFC-125 which forms an azeotrope-like mixture with FC-116 and which is hard to separate therefrom by distillation.

Specific examples of the fluorine-containing unsaturated compounds that can be removed by these adsorbents include at least one compound selected from a group consisting of tetrafluoroethylene, trifluoroethylene, 1,1-difluoroethylene, 1,2-difluoroethylene and monofluoroethylene, among which at least one compound selected from tetrafluoroethylene, trifluoroethylene and 1,1-difluoroethylene is preferable.

Molecular diameters of FC-116 as an objective product and the HFCs as impurities are calculated as follows: FC-116 has the molecular diameter of about 4.3 Å; whereas, for example, HFC-134a has the molecular diameter of about 4.2 Å and HFC-125 about 4.2 Å. Thus, differences are small between the molecular diameters of FC-116 and the HFCs of impurities. Accordingly, it was presumed that it was difficult to selectively adsorptively remove the HFCs present in FC-116 therefrom by only the differences of molecular diameter.

The inventors thus conducted extensive and intensive studies on the method for selectively adsorptively removing the HFCs by changing types of adsorbents and conditions of adsorption treatment, taking the polarities and pore sizes of adsorbent into consideration. As a consequence, the inventors found that when the adsorption operation was carried out, particularly, by using zeolites having the mean micropore size in the range of 3.5 Å to 11 Å and the silicon/aluminum ratio of not more than 1.5, for example, a zeolite having the mean micropore size of about 4.2 Å and the silicon/aluminum ratio of not more than 1.5, the content of the HFCs was able to be decreased in FC-116 initially containing approximately 500 ppm of the HFCs as impurities and that high-purity FC-126 containing only 10 ppm or less of the HFCs of impurities was able to be obtained by properly selecting types of the zeolites. Specifically, the preferable examples of the zeolite to be used in the present invention include MS-5A having a silicon/aluminum ratio of 1.0. MS-10X having a silicon/aluminum ratio of 0.81 and MS-13X having a silicon/aluminum ratio of 0.81.

With use of zeolites having the mean micropore size of less than 3.5 Å, for example, the mean micropore size of approximately 3.2 Å, though having the silicon/aluminum ratio (Si atoms/Al atoms) of not more than 1.5, no decrease is recognized in the content of the HFCs.

With use of zeolites having the mean micropore size over 11 Å though having the silicon/aluminum ratio (Si atoms/Al atoms) of not more than 1.5, no decrease is recognized in the content of the HFCs.

With use of zeolites having the silicon/aluminum ratio (Si atoms/Al atoms) over 1.5 though having the mean micropore size in the range of 3.5 Å to 11 Å, no decrease is recognized in the content of the HFCs.

Similar investigation was conducted with carbonaceous adsorbents (molecular sieving carbons) having the mean micropore size in the range of 3.5 Å to 11 Å, for example, with carbonaceous adsorbents having the mean micropore size of about 4 Å or about 5 Å, and it was recognized that the content of the HFCs was able to be decreased thereby. Further, it was also recognized that the content of the fluorine-containing unsaturated compounds contained in FC-116 can be decreased by the carbonaceous adsorbents. Therefore the contents of the HFCs and the fluorine-containing unsaturated compounds can be decreased simultaneously by using a mixture of the carbonaceous adsorbent and the zeolite.

With use of carbonaceous adsorbents having the mean micropore size over 11 Å, no decrease is recognized in the HFCs, and, for example, with use of active carbon having strong adsorptive capability and the mean micropore size of about 35 Å, popularly used, little decrease is recognized in the HFCs.

There is no specific limitation on a concentration of the HFCs of impurities contained in FC-116 before purified by the method of the present invention, but the concentration is preferably not more than 1 vol % (10,000 ppm) and more preferably not more than 0.1 vol % (1,000 ppm). Further, there is no specific limitation on a concentration of the fluorine-containing unsaturated compounds existing as impurities in FC-116, but the concentration is preferably not more than 0.1 vol % and more preferably not more than 0.01 vol %.

There is no specific limitation on the lower limit of the concentration either, but the method of the present invention is suitable for purification of FC-116 in which the concentration of the HFCs of impurities is preferably between 0.1 ppm and 10,000 ppm, whereby high-purity FC-116 in which the concentration of the HFCs of impurities is preferably not more than 1000 ppm can be obtained.

An example of the method for producing FC-116 as an objective product is the direct fluorination method for letting the fluorine gas react with the hydrofluorocarbon containing two carbon atoms in a molecule as described previously, and a concentration of chlorine compounds contained in the hydrofluorocarbon of raw material is preferably not more than 0.5 vol % and more preferably not more than 0.1 vol %.

In the purification method of FC-116 according to the present invention, no limitation is imposed on the method tar making the FC-116 containing the HFCs of impurities contact the adsorbent, and the contact method may be, for example, either a method of contact in vapor phase or a method of contact in liquid phase. Among them, the method of contact in liquid phase is more efficient and preferred.

The method of contact in liquid phase may be one of known methods such as the batch type, the continuous type or the like. From the industrial aspect, it is common practice to employ a method for, for example, providing at least two fixed bed type adsorption towers filled with the adsorbent according to the present invention, switching a tower under operation to another tower when the tower under operation reaches saturation adsorption, and regenerating the former.

In the purification method of FC-116 according to the present invention, no specific limitation is imposed on the treatment temperature, treatment amount, and treatment pressure upon contact of FC-116 containing the HFCs of impurities with the adsorbent, but preferred treatment temperatures are low temperatures; normally, for example, temperatures of −30° C. to 70° C. are preferred. The treatment pressure in the case of the liquid phase may be one capable of maintaining the liquid phase; the treatment pressure in the case of the vapor phase is not limited particularly.

EXAMPLES

The present invention will be described in further detail by examples and comparative examples, but it is noted that the present invention is by no means intended to be limited to the examples and may involve all changes and modificatione thereof within the scope not departing from the spirit of the present invention.

Production Example 1 of FC-116

The direct fluorination reaction was carried out while diluting 1,1-difluoroethane ($CHF_2CH_3$) and fluorine gas ($F_2$) with nitrogen gas and the reaction gas was introduced into an alkali cleaning column to remove hydrogen fluoride (HF) produced and a small amount of unreacted fluorine gas ($F_2$). The FC-116-rich product gas was purified by the known method of fractional distillation, then analyzed by gas chromatography. Thus obtained FC-116 (stock example 1) had the following composition.

|  | (unit: vol %) |
|---|---|
| $CF_3CF_3$ | 99.9588 |
| $CF_3CHF_2$ | 0.0316 |
| $CF_3CH_2F$ | 0.0067 |
| $CHF_2CHF_2$ | 0.0012 |
| $CF_3CH_3$ | 0.0008 |
| $CHF_3$ | 0.0007 |
| the rest | 0.0002 |

Production Example 2 of FC-116

1,1,1,2-tetrafluoroethane ($CF_3CH_2F$) [Ecoloace 134a (trade name: available from Showa Denko K. K., the purity of which was not less than 99.99%, which contained approximately 20 ppm of isomer $CHF_2CHF_2$, and from which no chlorine compound was detected], now supplied as a substitute for CFC-12 ($CCl_2F_2$), was used.

The direct fluorination reaction was carried out while diluting this Ecoloace 134a and fluorine gas ($F_2$) with nitrogen gas, the reaction gas was introduced into the alkali cleaning column to remove the hydrogen fluoride (HF) produced and a small amount of unreacted fluorine gas ($F_2$), the FC-116-rich product gas was purified by the known method of fractional distillation, then analyzed by gas chromatography. Thus obtained FC-116 (stock example 2) had the following composition.

|  | (unit: vol %) |
|---|---|
| $CF_3CF_3$ | 99.9828 |
| $CF_3CHF_2$ | 0.0154 |
| $CF_3CH_2F$ | 0.0012 |
| the rest | 0.0006 |

Production Example 3 of FC-116

The direct fluorination reaction was carried out while diluting pentafluoroethane($CF_3CHF_2$) and fluorine gas ($F_2$) with nitrogen gas, then reaction gas was introduced into an alkali cleaning column to remove hydrogen fluoride (HF) produced in the reaction and a small amount of unreacted fluorine gas ($F_2$). The FC-116-rich product gas was purified by the known method of fractional distillation, and then analyzed by gas chromatography. Thus obtained FC-116 (stock example 3) had the following composition.

|  | (unit: vol %) |
|---|---|
| $CF_3CF_3$ | 99.9833 |
| $CF_3CHF_2$ | 0.0106 |
| $CF_2=CF_2$ | 0.0032 |
| $CF_2=CHF$ | 0.0022 |
| $CH_2=CF_2$ | 0.0004 |
| the rest | 0.0003 |

Example 1

A stainless steel cylinder of volume 200 ml was charged with 20 g of a zeolite [molecular sieve 5A (available from Union Showa K. K.: the mean micropore size 4.2 Å, the silicon/aluminum ratio=1)], it was dried by vacuum drying, and thereafter approximately 80 g of FC-116 of stock example 1 was charged into the cylinder while cooling it. The cylinder was kept at the temperature of −20° C. for about eight hours with sometimes stirring the inside. After that, the liquid part was analyzed by gas chromatography. The detection limit of the HFCs by gas chromatography is approximately 1 ppm.

The result is as follows.

|  | (unit: vol %) |
|---|---|
| $CF_3CF_3$ | 99.9990 |
| $CF_3CHF_2$ | 0.0002 |
| $CF_3CH_2F$ | <0.0001 |
| $CHF_2CHF_2$ | <0.0001 |
| $CF_3CH_3$ | 0.0002 |
| $CHF_3$ | 0.0001 |
| the rest | 0.0003 |

As apparent from the above result, the content of the HFCs in FC-116 was able to be decreased by using the zeolite having the mean micropore size of 4.2 Å and the silicon/aluminum ratio of 1 as an adsorbent, and the content thereof was decreased to not more than 10 ppm.

Example 2

The stainless steel cylinder of volume 200 ml was charged with 20 g of the zeolite [molecular sieve 5A (available from Union Showa K. K.: the mean micropore size 4.2 Å, the silicon/aluminum ratio=1)], it was dried by vacuum drying, and thereafter approximately 80 g of FC-116 of stock example 2 was charged into the cylinder while cooling it. The cylinder was kept at the temperature of −20° C. for about eight hours with sometimes stirring the inside. After that, the liquid part was analyzed by gas chromatography.

The result is as follows.

|  | (unit: vol %) |
| --- | --- |
| $CF_3CF_3$ | 99.9995 |
| $CF_3CHF_2$ | 0.0001 |
| $CF_3CH_2F$ | <0.0001 |
| the rest | 0.0003 |

As apparent from the above result, the content of the HFCs in FC-116 was able to be decreased by using the zeolite having the mean micropore size of 4.2 Å and the silicon/aluminum ratio of 1, and the content was decreased to not more than 10 ppm.

Example 3

The stainless steel cylinder of volume 200 ml was charged with 20 g of a zeolite [molecular sieve 13X (available from Union Showa K. K.: the mean micropore size 10 Å, the silicon/aluminum ratio=0.81)], it was dried by vacuum drying, and thereafter approximately 80 g of FC-116 of stock example 2 was charged into the cylinder while cooling it. The cylinder was kept at room temperature for about eight hours with sometimes stirring the inside. After that, the liquid part was analyzed by gas chromatography.

The result is as follows.

|  | (unit: vol %) |
| --- | --- |
| $CF_3CF_3$ | 99.9964 |
| $CF_3CHF_2$ | 0.0028 |
| $CF_3CH_2F$ | 0.0006 |
| the rest | 0.0002 |

As apparent from the above result, the content of the HFCs in FC-116 was able to be decreased by using the zeolite having the mean micropore size of 10 Å and the silicon/aluminum ratio of 0.81.

Example 4

The stainless steel cylinder of volume 200 ml was charged with 20 g of an adsorbent that was a mixture of 10 g of the zeolite [molecular sieve 13X (available from Union Showa K. K.: the mean micropore size 10 Å, the sillcon/aluminun ratio=0.81)] and 10 g of the carbonaceous adsorbent [molecular sieving carbon available from Takeda Chemical Industries, Ltd.: the mean micropore site 5 Å], it was dried by vacuum drying, and thereafter approximately 80 g of FC-116 of stock example 2 was charged into the cylinder while cooling it. The cylinder was kept at room temperature for about eight hours with sometimes stirring the inside. After that, the liquid part was analyzed by gas chromatography.

The result is as follows.

|  | (unit: vol %) |
| --- | --- |
| $CF_3CF_3$ | 99.9961 |
| $CF_3CHF_2$ | 0.0031 |
| $CF_3CH_2F$ | 0.0006 |
| the rest | 0.0002 |

As apparent from the above result, the content of the HFCs in FC-116 was able to be decreased by using the adsorbent of the mixture of the zeolite having the mean micropore size of 10 Å and the silicon/aluminum ratio of 0.81 and the carbonaceous adsorbent having the mean micropore size of 5 Å.

Example 5

The stainless steel cylinder of volume 200 ml was charged with 20 g of an adsorbent that was a mixture of 10 g of the zeolite [molecular sieve 5A (available from union Showa K. K.: the mean micropore size 4.2 Å, the silicon/aluminum ratio=1.0)] and 10 g of the carbonaceous adsorbent [molecular sieving carbon available from Takeda Chemical Industries, Ltd.: the mean micropore size 4 Å], it was dried by vacuum drying, and thereafter approximately 80 g of FC-116 of stock example 3 was charged into the cylinder while cooling it. The cylinder was kept at room temperature for about eight hours with sometimes stirring the inside. After that, the liquid part was analyzed by gas chromatography.

The result is as follows.

|  | (unit: vol %) |
| --- | --- |
| $CF_3CF_3$ | 99.9987 |
| $CF_3CHF_2$ | 0.0008 |
| $CF_2=CHF$ | 0.0002 |
| the rest | 0.0003 |

As apparent from the above result, the content of the HFCs and the fluorine-containing unsaturared compounds in FC-116 was able to be decreased by using the adsorbent of the mixture of the zeolite having the mean micropore size of 4.2 Å and the silicon/aluminum ratio of 1.0 and the carbonaceous adsorbent having the mean micropore size of 4 Å.

Comparative Example 1

The stainless steel cylinder of volume 200 ml was charged with 30 g of a zeolite [molecular sieve XH-9 (available from Union Showa K. K.: the mean micropore size 3.2 Å, the silicon/aluminum ratio=1)], it was dried by vacuum drying, and thereafter approximately 80 g of FC-116 of stock example 2 was charged into the cylinder while cooling it. The cylinder was kept at the temperature of −20° C. for about ten hours with sometimes stirring the inside. After that, the liquid part was analyzed by gas chromatography.

The result is as follows.

|  | (unit: vol %) |
| --- | --- |
| $CF_3CF_3$ | 99.9829 |
| $CF_3CHF_2$ | 0.0153 |

-continued

| | (unit: vol %) |
|---|---|
| $CF_3CH_2F$ | 0.0012 |
| the rest | 0.0006 |

As apparent from the above result, no reduction of the content of the HFCs in FC-116 was recognized by use of the zeolite having the mean micropore size of less than 3.5 Å and the silicon/aluminum ratio of 1.

Comparative Example 2

The stainless steel cylinder of volume 200 ml was charged with 30 g of a zeolite [H-ZSM-5 (available from N.E. CHEMCAT CORP.: the mean micropore size 6 Å, the silicon/aluminum ratio=15)] (which is a zeolite equivalent to that used in Example VI in U.S. Pat. No. 5,523,499), it was dried by vacuum drying, and thereafter approximately 80 g of FC-116 of stock example 2 was charged into the cylinder while cooling it. The cylinder was kept at the temperature of −20° C. for about ten hours with sometimes stirring the inside. After that, the liquid part was analyzed by gas chromatography.

The result is as follows.

| | (unit: vol %) |
|---|---|
| $CF_3CF_3$ | 99.9852 |
| $CF_3CHF_2$ | 0.0134 |
| $CF_3CH_2F$ | 0.0010 |
| the rest | 0.0004 |

As apparent from the above result, no reduction of the content of the HFCs in FC-116 was recognized by use of the zeolite having the silicon/aluminum ratio of more than 1.5 though having the mean micropore size of 6 Å.

Comparative Example 3

The stainless steel cylinder of volume 200 ml was charged with 30 g of a zeolite [H-ZSM-5 (available from N.E. CHEMCAT CORP.: the mean micropore size 6 Å, the silicon/aluminum ratio=75)], it was dried by vacuum drying, and thereafter approximately 80 g of FC-116 of stock example 2 was charged into the cylinder while cooling it. The cylinder was kept at the temperature of −20° C. for about ten hours with sometimes stirring the inside. After that, the liquid part was analyzed by gas chromatography.

The result is as follows.

| | (unit: vol %) |
|---|---|
| $CF_3CF_3$ | 99.9841 |
| $CF_3CHF_2$ | 0.0143 |
| $CF_3CH_2F$ | 0.0012 |
| the rest | 0.0004 |

As apparent from the above result, no reduction of the content of the HFCs in FC-116 was recognized by use of the zeolite having the silicon/aluminum ratio of more than 1.5 though having the mean micropore size of 6 Å.

It was very difficult heretofore to remove the HFCs by purifying FC-116 containing the impurities of the HFCs including two carbon atoms in a molecule, but the purification method of FC-116 according to the present invention permits us to produce high-purity FC-116 used for dry etching of semiconductor by readily, economically, and industrially advantageously removing the HFCs.

The present invention employs a zeolite having the mean micropore size in the range of 3.5 Å to 11 Å and the silicon/aluminum ratio of not more than 1.5 or a mixutre comprising the above-described zeolite and a carbonaceous adsorbent (molecular sieving carbon) having the mean micropore size in the range of 3.5 Å to 11 Å as an adsorbent and involves making this adsorbent contact FC-116 containing the impurities of HFCs, thereby selectively adsorptively removing the HFCs so as to readily reduce the content of the HFCs. The present invention also enables us to produce high-purity FC-116 in which the content of the HFCs is 10 ppm or less, by properly selecting the type of the adsorbent.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A method for purifying hexafluoroethane, said method characterized in making hexafluoroethane containing impurities mainly including hydrofluorocarbons having two carbon atoms in a molecule contact a zeolite having a mean micropore size within a range of 3.5 Å to 11 Å and having a silicon/aluminum ratio of not more than 1.5 in a liquid phase so as to reduce said hydrofluorocarbons, wherein the hexafluoroethane containing impurities mainly including hydrofluorocarbons having two carbon atoms in a molecule is produced by a direct fluorination method for letting fluorine gas react with a hydrofluorocarbon having two carbon atoms in a molecule.

2. A method for purifying hexafluoroethane according to claim 1, wherein said hexafluoroethane is made to contact an absorbent formed by adding to said zeolite a carbonaceous absorbent having a mean micropore size within a range of 3.5 Å to 11 Å.

3. A method for purifying hexafluoroethane according to claim 2, wherein a ratio by weight of the zeolite to the carbonaceous absorbent is not less than 1.0.

4. A method for purifying hexafluoroethane according to claim 1, wherein said hydrofluorocarbons are at least one compound selected from the group consisting of fluoroethane, 1,1-difluoroethane, 1,1,1-trifluoroethane, 1,1,1,2-tetrafluoroethane, 1,1,2,2-tetrafluoroethane, and pentafluoroethane.

5. A method for purifying hexafluoroethane according to claim 2, wherein said hydrofluorocarbons are at least one compound selected from the group consisting of fluoroethane, 1,1-difluoroethane, 1,1,1-trifluoroethane, 1,1,1,2-tetrafluoroethane, 1,1,2,2-tetrafluoroethane, pentafluoroethane, tetrafluoroethylene, trifluoroethylene, 1,1-difluoroethylene, 1,2-difluoroethylene and monofluoroethylene.

6. A method for purifying hexafluoroethane according claim 1, wherein a content of the hydrofluorocarbons having two carbon atoms in a molecule is not more than 10 ppm in the hexafluroethane purified by said method.

7. A method for purifying hexafluoroethane according to claim 2, wherein a content of the hydrofluorocarbons having two carbon atoms in a molecule is not more than 10 ppm in the hexafluroethane purified by said method.

8. A method for purifying hexafluoroethane according claim 1, wherein said zeolite is at least one selected from MS-5A, MS-10X and MS-13X.

9. A method for purifying hexafluoroethane according claim 2, wherein said zeolite is at least one selected from MS-5A, MS-10X and MS-13X.

* * * * *